United States Patent [19]

Behan et al.

[11] Patent Number: 5,676,163

[45] Date of Patent: Oct. 14, 1997

[54] ANTI-SMOKE PERFUMES AND COMPOSITIONS

[75] Inventors: John Martin Behan, Kennington; Julie Anne Goodall, Ashford; Keith Douglas Perring, Kent; Christopher Charles Piddock, Kent; Alan Forbes Provan, Kent, all of Great Britain

[73] Assignee: Quest International BV, Naarden, Netherlands

[21] Appl. No.: 647,963

[22] PCT Filed: Nov. 23, 1994

[86] PCT No.: PCT/EP94/03882

§ 371 Date: May 30, 1996

§ 102(e) Date: May 30, 1996

[87] PCT Pub. No.: WO95/15186

PCT Pub. Date: Jun. 8, 1995

[30] Foreign Application Priority Data

Nov. 30, 1993 [EP] European Pat. Off. ............. 93309567
Mar. 31, 1994 [EP] European Pat. Off. ............. 94302324

[51] Int. Cl.$^6$ ........................................................ A24F 3/02
[52] U.S. Cl. .......................... 131/213; 131/334; 426/533; 426/534; 568/592
[58] Field of Search ........................... 131/2, 17 R, 144, 131/365, 243, 334; 426/533, 534; 568/592

[56] References Cited

U.S. PATENT DOCUMENTS 4,036,237  7/1977  Teng ............................................. 131/17
5,320,131  6/1994  Dull ............................................. 131/365

FOREIGN PATENT DOCUMENTS 316 726   5/1989  European Pat. Off. .
401 140  12/1990  European Pat. Off. .
430 315   6/1991  European Pat. Off. .
535 942   4/1993  European Pat. Off. .
2 666 510 3/1992  France .

OTHER PUBLICATIONS

Patent Abstracts of Japan, vol. 012, No. 297, (C–519), Aug. 12, 1988 & JP,A,63 066115, Mar. 24, 1988, see abstract.

Database WPI, Section Ch, Week 8530, Derwent Publications Ltd., Class D21, AN 85–181161 & JP,A,60 109 512, Jun. 15, 1986, see abstract.

*Primary Examiner*—Terressa Mosley
*Attorney, Agent, or Firm*—Cushman Darby & Cushman IP Group Pillsbury Madison & Sutro LLP

[57] ABSTRACT

The invention is concerned with a process for counteracting smoke malodour wherein enclosed air spaces wherein smoke maladour is present, or substrates on which smoke malodour has deposited are brought in contact with one or more perfumery aldehydes of the class I according to general structure, wherein R1 and R2 each may be: hydrogen, alkyl, hydroxyl or alkoxy, or together may be methylenedioxy or with a perfume containing such aldehydes. Preferably the perfume also contains one or more perfumery aldehydes of class according to general structure, wherein R1 is a phenyl ring optionally substituted with an alkyl group, R2 represents hydrogen or both R2 taken together represent a double bond, and R3 is hydrogen or an alkyl chain with 1 to 6 carbon atoms. The smoke malodour counteracting perfumes preferably contain at least 3.5% w/w of class I aldehydes and at least 10% w/w of class II aldehydes. The perfumes are suitable for incorporation in air fresheners, and products for treatment or cleaning of skin, hair, clothing, curtains, wall paper and floor cover.

16 Claims, No Drawings

ANTI-SMOKE PERFUMES AND COMPOSITIONS

This application claims benefit of international application PCT/EP94/03882, filed Nov. 23, 1994.

This invention is concerned with the use of certain perfume ingredients to counteract smoke malodours, particularly tobacco smoke malodour. The invention also relates to perfumes and products which incorporate such perfume ingredients.

The problem of malodours has been recognised for many years, and numerous methods have been developed to overcome these where they occur. Perfumes are commonly used as malodour counteractants either alone or in combination with other materials such as absorbents, oxidants and other actives.

Perfumes generally have some capability to neutralise a wide variety of malodours, this effect arising in large part from the phenomenon of 'odour masking' wherein the perfume intensity is sufficiently high to swamp or distort the olfactory perception of malodour. Often, however, the dosage levels of perfume required to obtain effective masking are outside the dosage levels preferred by product formulators and liked by customers.

On the other hand, it is known that certain perfumes are surprisingly effective against specific malodours, and this activity is not explainable only in terms of odour masking. For example, GB 2016507, U.S. Pat. No. 4,134,838, U.S. Pat. No. 4,663,068, GB 2013493 and EP 404470 all describe perfumes which offer deodorant activity against body odour when incorporated into various products (eg soap, fabric treatment products, skin products). Likewise, perfumes are known which are effective against a range of other malodours, but perfumes which have high activity against smoke malodour are rare, and no methods have been reported for creating such perfumes in a structured manner. Thus, deodorant perfumes created according to the guidelines described in the patents referenced above would not appear to be significantly more efficacious against smoke malodour than any randomly chosen perfume would be by odour masking.

EP-A-0 401 140 describes mixtures of aldehydes which can produce good general deodorancy, embodiments of the invention being aerosol airfresheners and disinfectant liquids perfumed solely with such aldehyde mixtures. The majority of common perfume aldehydes are included within the broad definitions given, but the most key mixtures cited were based on helional (2-methyl-3-(3',4'-methylenedioxyphenyl)propanal), citral, citronellal and jasmonal (α-amylcinnamic aldehyde).

FR 2666510 discloses deodorising compositions designed to counteract malodours from many disparate sources, e.g. animal and vegetable sources, industrial processes, drains, and tobacco combustion. A number of perfume aldehydes, alcohols and esters together with recommended dosages are detailed, among which citral and phenyl-acetaldehyde were key components. One further component, described as a 'chemical molecule' (as distinct presumably from similar materials used in perfumery) was required to be present, preferably in at least 5% by weight of the composition; the sole example of this class was the straight chain aldehyde heptanal. Several airfreshening product formulations were disclosed as embodiments of the invention.

EP-A-0 247 946 describes perfumes for counteracting the malodour of animal excretions or excrements containing perfume ingredients with a vapour pressure below 4 Pa at 25° C. Initially a whole list of the most diverse known perfume ingredients are mentioned as suitable, but on further reading of the specification it becomes clear that only a limited number of compounds of various chemical classes are preferred among which helional as the only aldehyde.

Although in the references mentioned above counteraction of malodours appears to be intended, it is often not clear whether real counteraction is involved or whether the perfumes described therein merely have a masking effect, since a true comparison with other perfumes, without the claimed components is often lacking.

Other methods for combatting smoke which do not rely upon the use of perfume ingredients are of course known, e.g. filtration of air through filters in air-conditioners, or the use of absorbents such as the anti-tobacco candle described in FR 2593398. However, such methods produce Useful benefits only by intercepting smoke particles and smoke constituents before these malodorants impinge on substrates such as skin, hair, curtains and clothes.

The build up of malodour on clothes or on skin or hair is one example of the widespread malodour problem associated with smoke. This particularly applies in the case of tobacco smoke i.e. to people who smoke cigarettes, pipes, or cigars etc, and of course also to public environments where smoking occurs. The present invention addresses this problem.

The invention concerns a process for counteracting smoke malodours by bringing enclosed air spaces wherein smoke malodour is present, or substrates on which smoke malodour has deposited in contact with certain perfumery aldehydes and mixtures thereof to counteract smoke malodour. Thus, the invention relates to the use of such perfumery aldehydes, and perfumes containing them, for counteracting smoke malodour. Such perfumes are developed for incorporation in airfresheners and in products for treating substrates on which smoke malodour has deposited.

Thus, perfumery aldehydes which have been found to very effectively counteract tobacco odour are those of the class according to the general structure I shown below:

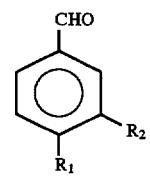

wherein R1 and R2 each may be: hydrogen, alkyl, hydroxyl or alkoxy, or together may be methylenedioxy. Such aldehydes are hereinafter referred to as "class I aldehydes".

Examples of such class I aldehydes are: anisic aldehyde, o-allyl-vanillin, benzaldehyde, cuminic aldehyde, ethyl-aubepin, ethyl-vanillin, heliotropin, tolyl aldehyde, and vanillin. Particularly preferred are: anisic aldehyde, benzaldehyde, cuminic aldehyde, ethyl-aubepin, ethyl-vanillin, heliotropin and vanillin.

Malodour counteracting perfumes should contain at least 3% of w/w class I aldehydes, preferably at least 3.5%, more preferably at least 4%, most preferably at least 5.5%.

A second class of aldehydes has been found which, while not themselves exhibiting the high activity shown by the class I aldehydes, may usefully be included in compositions in combination with the class I aldehydes, and act synergistically with them leading to high smoke malodour counteraction at lower incorporation levels of class I aldehydes in the perfume. These are the aldehydes according to the general structure II shown below:

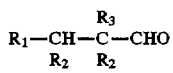

wherein R1 is a phenyl ring optionally substituted with an alkyl group, R2 represents hydrogen or both R2 taken together represent a double bond, and R3 is hydrogen or an alkyl chain with 1 to 6 carbon atoms, preferably 1 to 3 carbon atoms. Such aldehydes are hereinafter referred to as "class II aldehydes".

Examples of class II aldehydes are:

3-(4'-tert.butylphenyl)propanal, 2-methyl-3-(4'-tert.butylphenyl)propanal, 2-methyl-3-(4'-isopropylphenyl) propanal, 2,2-dimethyl-3-(4-ethylphenyl)propanal, cinnamic aldehyde, α-amyl-cinnamic aldehyde, and α-hexyl-cinnamic aldehyde.

Malodour counteracting perfumes should preferably contain at least 10% w/w. class II aldehydes, more preferably at least 15%. In perfumes containing such amounts of class II aldehydes a desired degree of malodour counteractant efficacy may be obtained with a lower amount of class I aldehydes than would be possible without the presence of class II aldehydes.

In contrast to the aldehydes of the classes I and II according to the invention, aliphatic aldehydes such as dodecanal and decanal were found to have little effect in smoke malodour counteraction in spite of the fact that they are extremely potent odorants and mentioned in EP-A-0 401 140 as preferred general malodour counteractant aldehydes. Also class II compound Jasmonal (amyl-cinnamic aldehyde) alone has little effect in counteracting smoke malodour in spite of being mentioned as preferred general malodour counteractant in EP-A-0 401 140.

The composition of smoke from burning tobacco has been studied extensively, and there exists ample literature which lists the hundreds of components to be found. For example, Stedman's comprehensive review of the early literature can be found in Chem. Rev., volume 68, 153–207 (1967). This literature clearly reveals that many types of chemical classes are present in tobacco smoke, the exact composition varying according to the nature of the tobacco, its processing, the presence of additional materials, and the conditions under which it burns. Acids, bases, hydrocarbons, nitriles, phenols, terpenes, sulphur compounds and many other classes have been detected. However, not all these materials will play a major role in the overall smoke malodour, particularly after smoke malodour deposition has occurred, i.e. following transport of the malodorous materials to a substrate such as skin, hair or fabric. Certain materials will be substantive to the substrate, other materials will change chemically over time, and the balance of materials which are key to malodour control needs to be well understood for optimal counteraction.

We have found that nitrogenous materials present in tobacco smoke, including such powerful odorants as pyrazines, alkylpyridines and vinylpyridines, deposit on hair easily, and are present in significant proportions in the headspace above smoke-exposed hair. Without being bound by theory it is believed that certain aldehydes possess the right combination of physicochemical and olfactive properties to enable them to counteract such nitrogenous materials effectively, particularly in the context of tobacco odour. Various processes may be involved, including chemical reactions, e.g. between the nitrogen compounds and acids formed from the aldehydes by air oxidation.

However, there are also many other malodorants present in smoke, and for optimal counteraction it may be desirable to add perfume ingredients which are effective against these. Depending upon the composition of the smoke, on 'screening' factors such as deposition on substrate and subsequent physical and chemical changes and on desired overall odour character of the perfume, there will be an optimal balance between adding more key aldehydes and adding other (perfume) ingredients which may offer more general but less specific malodour counteraction and/or the right fragrance properties. It has been found that the inclusion of at least 4% of class I aldehydes, preferably at least 5.5%, within a perfume can provide a reduction of perceived tobacco malodour in use of at least 50%, whilst minimising restrictions on perfume creation and design. In the presence of at least 10% w/w, preferable at least 15%, of class II aldehydes the minimum amount of class I aldehydes required for a reduction of at least 50% in perceived tobacco malodour is reduced to 3.5% w/w of the perfume.

Perfumes according to the invention can be used in air-fresheners and in products for treatment or cleaning of substrates which have been in contact with smoke and on which smoke malodour has therefore been deposited. Examples of such substrates are skin, hair, clothing, curtains, wallpaper, carpets and other floor cover materials. Depending on the type of product, it may contain between 0.05 and 90% w/w of perfume according to the invention, preferably between 0.1 and 40%.

For the purposes of this invention a perfume is defined as a mixture of perfume ingredients, if desired mixed with or dissoved in a suitable solvent or mixed with a solid substrate, which is used to impart a desired odour to the the products mentioned above. Such perfume ingredients are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials - 1991", Allured Publishing Co. Wheaton, Ill. USA. They may include natural products such as extracts, essential oils, absolutes, resinoids, resins, concretes etc., but also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds.

The smoke malodour counteraction of the aldehydes according to the invention and the perfumes containing them is illustrated in the following examples.

EXAMPLE 1

The headspace reduction of nitrogenous smoke components using the perfumery aldehydes according to the invention was demonstrated as described below, using a nitrogen-specific detector to specifically monitor the nitrogen compounds:

Two hair switches (dry hair weight 8 g each) were washed with unperfumed shampoo (composition 1, see below) and exposed to cigarette smoke following the procedures detailed below. Following smoke exposure, the switches were allowed to equilibrate in air for 15 minutes. One of the switches was treated with 0.6 g of a hair cologne product (composition 2, see below) containing 2% of a perfume based mainly on aldehydes (composition 3, see below). Headspace analysis was carried out on each switch using standard trapping techniques [as described by Nunez, Gonzales and Janak in J. Chromatography volume 300, 127–162 (1984)]. Eicosane was added as an internal standard prior to gas chromatography. Analysis of the samples was carried out on a Varian 3400 gas chromatograph equipped with two detectors in parallel: a flame ionisation detector (FID) and a thermionic specific detector (TSD)

tuned to nitrogen. A tentative identification of the peaks in the TSD output is as follows:

| Peak: | Component: |
|---|---|
| 1 | Pyrazine |
| 2 | Pyridine |
| 3 | Pyrrole |
| 4 to 6 | Methyl-pyridines |
| 7 | 2,3-Dimethyl-pyridine |
| 8 | 2,4- and 2,5-Dimethyl- pyridine |
| 9 | Vinyl-pyridine |
| 10 | Benzonitrile |
| 11 | Nicotine |

FIGS. 1 and 2 show the FID and TSD outputs for headspace samples taken from untreated smoked hair switches, whereas FIGS. 3 and 4 show these outputs for the smoked hair switches treated with hair cologne containing a perfume according to the invention. A comparison of these figures clearly show the reduction in the concentrations of key nitrogen-containing components of tobacco malodour in the head space above the treated hair switches.

Wash Procedure

Hair switches were rinsed in warm water (40° C.), then washed with shampoo base for 30 seconds (10% shampoo/ dry weight hair) and the lathered hair left to stand for 1 minute. The hair was then immersed repeatedly for 10 seconds into each of three beakers containing 600 ml warm water (40° C.). A final rinse (500 ml warm water) was slowly poured over the switch to remove any remaining shampoo. The hair was dried for one hour in a drying cabinet. Any remaining dampness was removed by use of a hairdryer.

Smoking Procedure

Two lit cigarettes were placed into a sealed oven and allowed to burn out (10 minutes). The oven was opened to clear excess smoke before the hair switches were placed inside and the oven resealed for 20 minutes.

| Composition 1: Shampoo base | | |
|---|---|---|
| Component | w/w % | Supplier: |
| Empicol ESB3 | 45.00% | Albright & Wilson |
| Tegobetaine L7 | 7.00% | Th Goldschmidt AG |
| Empilan CDE | 1.00% | Albright & Wilson |
| Sodium chloride | 0.70% | |
| Water | to 100% | |
| Citric acid | to pH 6–6.5 | |

| Composition 2: Hair cologne | |
|---|---|
| Alcohol | 40.0% |
| PEG 600 | 2.0% |
| Perfume | 2.0% |
| Water | to 100% |

| Composition 3: Perfume | |
|---|---|
| perfume ingredient | w/w % |
| Anisic aldehyde | 12.5%* |
| Benzaldehyde | 12.5%* |
| Vanillin | 6.25%* |
| Amylcinnamic aldehyde | 12.5%** |
| 2-methyl-3(4'-tert.butylphenyl) propanal | 12.5%** |
| Diethyl phthalate | 18.75 |
| Linalol | 12.5% |
| Styrallyl acetate | 12.5% |

*Class I aldehyde
**Class II aldehyde

EXAMPLE 2

The tobacco malodour counteraction of various perfumes in shampoo was measured using sensory analysis as described below.

Hair switches were washed with various perfumed shampoos and then subjected to the smoking procedure. The washed and smoked hair switches were subjected to sensory analysis, comparing them with unwashed smoked hair switches (CONTROL), as outlined below. Thus, the influence of the various perfumes on the perceived smoke malodour deposited on the hair was assessed. Perfumes A to F were used for perfuming the shampoo and thus sensorily tested for their ability to counteract smoke malodour. All hair switches, "washed" and "unwashed", before smoking were first washed in unperfumed shampoo to remove any initial odour the switches may have had.

The washing procedure was as outlined in Example 1, with the same perfume base. However, this time 0.5% of one of the perfumes A–F was added to each of the portions of the shampoo base. Also the smoking procedure outlined in Example 1 was used.

Sensory Analysis

The perceived intensity of residual malodour was assessed on the hair by a panel of 30 individuals, trained to use magnitude estimation as the sensory scaling technique, see Mailgaard, Civille and Carr, "Sensory Evaluation Techniques", CRC Press, 2nd edition 1991. The results were normalised using internal standards and averaged to give a consensus value for the perceived intensity of residual malodour on the switches for each shampoo perfume. These perceived intensities are expressed in arbitary units, which cannot be interpreted as absolute values of intensity, but are indicative of the ratio of perceived intensities of maledour for the tested perfume. The normalisation was carried out in such a way as to express the residual malodour as a percentage of the perceived malodour intensity of the CONTROL.

Systems where the malodour intensity were at least halved were rated as good. Ideally, the malodour intensity is reduced by 50% or over, and the perceived intensity of residual perfume is greater than that of the malodour.

Perfumes A to F were tested in a single experiment. The results demonstrate that the presence of class II aldehydes can improve the performance of class I aldehydes, even though they themselves are not sufficiently effective to halve the malodour level in the above test at levels of up to 10% in perfumes.

TABLE 1

| Perfume | Perceived Intensity of tobacco malodour* | Composition** I | II |
|---|---|---|---|
| Perfume A | 29 ⎤ | 4.85 | 0 |
| Perfume B | 37 ⎦ | 3.5 | 16.5 |
| Perfume C | 52 ⎤ | 3.5 | 6.5 |
| Perfume D | 58 ⎥ | 0 | 10 |
| Perfume E | 58 ⎦ | 0 | 10 |
| Perfume F | 68 | 0 | 10 |
| CONTROL | 100 | | |

*Expressed as a percentage of the CONTROL
**Amount of Class I and II aldehydes as percentage w/w of the total perfume
Note: the differences between values linked by the tie bars are not statistically significant at 95% confidence level.

In a separate experiment compositions G to J were created as equal intensity mixtures to test whether the perceived reduction of malodour intensity was predominantly or entirely caused by odour masking. Perfume intensities of the perfumed shampoos were also determined using magnitude estimation. Hair switches were washed and malodour reduction determined as outlined above.

TABLE 2

| Perfume | Perceived Intensity of tobacco malodour | Composition I | II | Perfume Intensity* |
|---|---|---|---|---|
| Perfume G | 41 | 5.7 | 19.3 | 108 |
| Perfume H | 67 | 0 | 0 | 106 |
| Perfume J | 72 | 0 | 0 | 105 |
| CONTROL | 100 | | | |

*Perceived perfume intensity of perfumed shampoo
Note: the differences between values linked by the tie bars are not statistically significant at 95% confidence level.

The superior performance of example g (which lies within the scope of the present invention) shows that besides malodour masking a genuine malodour counteraction takes place which is independent of the perfume intensity but caused by the presence of the class I and II aldehydes.

Perfume A

| | |
|---|---|
| Anisic aldehyde | 0.5%* |
| Benzaldehyde 10% DPG AA1423 | 0.5%* |
| Citronellol standard | 20.0% |
| Cuminic aldehyde | 0.1%* |
| Dipropylene glycol | 20.0% |
| Ethyl vanillin | 1.5%* |
| Geraniol standard | 0.7% |
| Heliotropin | 2.7%* |
| Linalol | 4.0% |
| Phenyl ethyl alcohol | 50.0% |

Perfume B

| | |
|---|---|
| Anisic aldehyde | 0.6%* |
| Benzyl acetate extra | 8.0% |
| Citronellol standard | 10.0% |
| Ethyl vanillin 10% DPG AA855 | 20.0%* |
| Geraniol standard | 15.0% |
| Heliotropin | 0.5%* |
| Hexyl cinnamic aldehyde | 10.0%** |
| Lily aldehyde | 6.5%** |
| Limonene dextro | 10.0% |
| Linalol | 4.0% |
| para Tolyl aldehyde | 0.2%* |
| Phenyl ethyl alcohol | 15.0% |
| Vanillin | 0.2%* |

Perfume C

| | |
|---|---|
| Anisic aldehyde | 0.5%* |
| Citronellol standard | 30.0% |
| Dipropylene glycol | 25.0% |
| Geraniol standard | 20.0% |
| Heliotropin | 2.5%* |
| Lily aldehyde | 6.5%** |
| Phenyl ethyl alcohol | 15.0% |
| Vanillin | 0.5%* |

Perfume D

| | |
|---|---|
| Dipropylene glycol | 10.0% |
| Geraniol standard | 2.5% |
| Lily aldehyde | 10.0%** |
| Limonene dextro | 5.0% |
| Linalol | 20.0% |
| Nerol standard | 2.5% |
| Phenyl ethyl alcohol | 38.0% |
| Tetrahydrolinalol | 2.0% |

Perfume E

| | |
|---|---|
| Amyl cinnamic aldehyde | 2.5%** |
| Citronellol standard | 5.0% |
| Cyclamen aldehyde | 0.5%** |
| Geraniol standard | 15.0% |
| Hexyl cinnamic aldehyde | 2.0%** |
| Lily aldehyde | 5.0%** |
| Linalol | 5.0% |
| Phenoxyethanol | 50.0% |
| Phenyl ethyl alcohol | 15.0% |

Perfume F

| | |
|---|---|
| Amyl cinnamic aldehyde | 0.5%** |
| Benzyl acetate extra | 10.0% |
| Bourgeonal | 0.5%** |
| Cyclamen aldehyde | 1.0%** |
| Dipropylene glycol | 20.0% |
| Geraniol standard | 10.0% |
| Hexyl cinnamic aldehyde | 2.0%** |
| Lily aldehyde | 1.5%** |
| Linalol | 30.0% |
| Phenyl ethyl alcohol | 20.0% |

Perfume G

| | |
|---|---|
| Amyl cinnamic aldehyde | 9.65%** |
| Citronellol | 17.25% |
| Heliotropin | 5.7%* |
| Lily aldehyde | 9.65%** |
| Linalol | 11.85% |
| Lixetone | 3.45% |
| Methyl ionone alpha iso | 5.775% |
| Orange Brazilian | 5.775% |
| Phenyl ethyl alcohol | 22.8% |
| Tetrahydrolinalol | 2.25% |
| Tonalid | 5.85% |

Perfume H

| | |
|---|---|
| Benzyl acetate | 5.0% |
| Citronellol | 17.25% |
| Linalol | 13.85% |
| Lixetone | 3.45% |
| Methyl ionone alpha iso | 7.025% |
| Orange Brazilian | 5.775% |
| Phenyl ethyl alcohol | 35.3% |
| Styrallyl acetate | 0.25% |
| Terpineol | 4.0% |
| Tetrahydrolinalol | 2.25% |
| Tonalid | 5.85% |

Perfume J

| | |
|---|---|
| Citronellol | 23.0% |
| Linalol | 15.8% |

-continued

| | |
|---|---|
| Lixetone | 4.6% |
| Methyl ionone alpha iso | 7.7% |
| Orange Brazilian | 7.7% |
| Phenyl ethyl alcohol | 30.4% |
| Tetrahydrolinalol | 3.0% |
| Tonalid | 7.8% |

KEY
*Class I aldehyde
**Class II aldehyde
Bourgeonal: 3-(4'-tert.butylphenyl)propanal
Cyclamen aldehyde: 2-methyl-3(4'-isopropylphenyl)
Lily aldehyde: 2-methyl-3(4'-tert.butylphenyl)propanal
Lixetone: acetyl cedrene
Tonalid: 1,1,2,4,4,7-hexamethyl-6-acetyl-tetralin

We claim:

1. A process for counteracting smoke malodors in an enclosed public air space or substrate subject to such malodors, which comprises contacting said space or support with an effective counteracting amount of one or more perfumery aldehydes of Formula I:

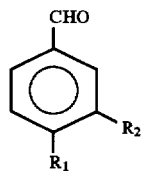

wherein $R_1$ and $R_2$ are each independently selected from the group consisting of hydrogen, alkyl, hydroxyl and alkoxy, or together comprise methylenedioxy, or with a perfume containing one or more of such aldehydes.

2. A process according to claim 1 wherein the perfume contains at least 3.5% of said aldehydes on a weight basis.

3. A process according to claim 2 wherein the perfume contains at least 4% of said aldehydes on a weight basis.

4. A process according to claim 1 wherein the space or the substrate is contacted with a mixture of one or more of said aldehydes and one or more perfumery aldehydes of Formula II below:

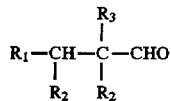

wherein $R_1$ is a phenyl ring optionally substituted with an alkyl group, $R_2$ represents hydrogen or both $R_2$ taken together represent a double bond, and $R_3$ is hydrogen or an alkyl chain with 1 to 6 carbon atoms, or with a perfume containing such mixture.

5. A process according to claim 4 wherein the perfume contains at least 3.5% of said Formula I aldehydes together with at least 10% of said Formula II aldehydes on a weight basis.

6. A process according to claim 5 wherein the perfume contains at least 15% of said Formula II aldehydes on a weight basis.

7. A process according to claim 1 wherein the Formula I aldehydes are chosen from the group consisting of: anisic aidehyde, o-allyl-vanillin, benzaldehyde, cuminic aidehyde, ethyl-aubepin, ethyl-vanillin, heliotropin, tolyl aidehyde, and vanillin.

8. A process according to claim 1 wherein the Formula I aldehydes are chosen from the group consisting of: anisic aidehyde, benzaldehyde, cuminic aldehyde, ethyl-aubepin, ethyl-vanillin, heliotropin and vanillin.

9. A process according to claim 4 wherein the Formula II aldehydes are chosen from the group consisting of: 3-(4'-tert. butyl-phenyl)propanal, 2-methyl-3-(4'-tert.butylphenyl) propanal, 2-methyl-3-(4'-isopropylphenyl)propanal, 2,2-dimethyl-3-(4'-ethylphenyl)propanal, cinnamic aldehyde, α-amyl-cinnamic aldehyde, and α-hexyl-cinnamic aldehyde.

10. A perfume for counteracting smoke malodor which comprises: at least 3.5% by weight of a perfumery aldehyde of Formula I

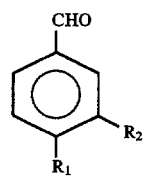

wherein $R_1$ and $R_2$ are each independently selected from the group consisting of: hydrogen, hydroxyl and alkoxy, or together are methylenedioxy; and at least 10% by weight of a perfumery aldehyde of Formula II

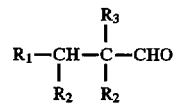

wherein $R_1$ is a phenyl ring optionally substituted with an alkoxy group, $R_2$ is hydrogen or both $R_2$ taken together represent a double bond and $R_3$ is hydrogen or an alkyl group with 1 to 6 carbon atoms.

11. A perfume according to claim 10 wherein the Formula I aldehydes are chosen from the group consisting of: anisic aidehyde, o-allyl-vanillin, benzaldehyde, cuminic aldehyde, ethyl-aubepin, ethyl-vanillin, heliotropin, tolyl aldehyde, and vanillin and wherein the Formula II aldehydes are chosen from the group consisting of: 3-(4'-tert.butylphenyl)-propanal, 2-methyl-3-(4'-tert.butylphenyl)propanal, 2-methyl-3-(4'-isopropylphenyl)propanal, 2,2-dimethyl-3-(4'-ethylphenyl)propanal, cinnamic aldehyde, α-amyl-cinnamic aldehyde, and α-hexyl-cinnamic aldehyde.

12. A product for treatment or cleaning of hair containing a perfume according to claim 11.

13. An air freshener containing a perfume according to claim 11.

14. A product for treatment or cleaning of skin containing a perfume according to claim 11.

15. A product for treatment or cleaning of clothing or curtains containing a perfume according to claim 11.

16. A product for treatment or cleaning of wall paper or floor cover containing a perfume according to claim 11.

* * * * *